United States Patent [19]

Härtl

[11] Patent Number: 5,178,178

[45] Date of Patent: Jan. 12, 1993

[54] VALVE ASSEMBLY

[75] Inventor: Hans-Georg Härtl, Wilmington, Del.

[73] Assignee: Hewlett-Packard Company, Palo Alto, Calif.

[21] Appl. No.: 725,953

[22] Filed: Jun. 27, 1991

Related U.S. Application Data

[63] Continuation-in-part of Ser. No. 638,304, Jan. 7, 1991, abandoned.

[51] Int. Cl.⁵ .......................................... F16K 11/044
[52] U.S. Cl. ..................................... 137/114; 137/112
[58] Field of Search ................ 137/111, 112, 113, 114

[56] References Cited

U.S. PATENT DOCUMENTS

| | | | |
|---|---|---|---|
| 2,024,548 | 12/1935 | Struve | 137/112 |
| 2,257,249 | 9/1941 | Thomas | 137/113 X |
| 3,612,086 | 10/1971 | Roth | 137/114 X |
| 3,779,267 | 12/1973 | Cowan | 137/113 X |
| 4,018,244 | 4/1977 | Burns | 137/113 |
| 4,354,518 | 10/1982 | Kuroda | 137/112 |

Primary Examiner—Alan Cohan
Attorney, Agent, or Firm—Richard F. Schuette

[57] ABSTRACT

A valve assembly is provided for controlling pressurized inputs from two separate fluid sources, and in particular to provide enhanced isolation between the sources and to buffer short-term fluctuations in fluid flow. A high pressure chamber is provided which is separated into two chamber portions by a fluid-impervious flexible membrane. A valve, such as a ball valve, having a movable member is positioned in an inlet port in each channel portion, fluid flowing, for a preferred enbodiment, from a fluid source under pressure through the inlet port of a chamber portion, an output port in the portion and a restrictor to a mixer. A pressure differential in the chamber portions deflects the diaphragm to bear against the movable member in the lower pressure chamber portion, closing the valve for this chamber portion before the pressure is sufficient to result in any backflow therethrough. The membrane also deflects when there are momentary breaks in the flow from one source to temporarily buffer flow from the other source, thus maintaining a substantially uniform mix ratio.

5 Claims, 2 Drawing Sheets

VALVE ASSEMBLY

CROSS REFERENCE TO RELATED APPLICATION

This application is a continuation-in-part of application Ser. No. 07/638,304, filed Jan. 7, 1991, now abandoned.

FIELD OF THE INVENTION

This invention relates to valve assemblies and more particularly to a valve assembly for controlling pressurized inputs from two separate fluid sources.

BACKGROUND OF THE INVENTION

In applications such as high pressure chromatography, it is necessary to mix two fluids, which fluids may be either liquids or gases, each of which is received from a high pressure source. Since the pressures under which fluids are delivered in such a system may be high, 6,000 psi. or higher in a super critical fluid chromatography (SFC) system, variations in pressure from the two sources can result in a number of potential problems.

A first problem is that it is necessary to isolate fluid being pumped from one source from fluid being pumped from the other source under situations where fluid is being delivered only from one of the sources, where both pumps are turned off, but where normal pressure from one source is greater than than that from the other, or in other situations where there is greater pressure from one source than from the other. Without such isolation, fluid from one source may contaminate the other source as a result of back flow into its supply line through the mixer, and it may be necessary to purge the line leading from the turned off or low pressure source or to prime its pump, both of which take time and reduce the operating efficiency of the system. Contamination, if not purged, can also result in erroneous measurements being taken, or other problems in the system.

It is also desirable that the flow of fluids into the mixer be substantially uniform regardless of slight flow fluctuations from the pumps. It is, therefore, desirable that such fluctuations be buffered to permit uniform fluid flow.

Systems do not currently exist for dealing with the problems indicated above in a high pressure fluid mixing environment.

SUMMARY OF THE INVENTION

It is, therefore, an object of this invention to provide an improved valve assembly for controlling pressurized inputs from two separate fluid sources which provides enhanced isolation between the sources, provides backflow protection, and which buffers short-term fluctuations in fluid flow between the fluid sources.

More particularly, this invention provides a valve assembly of the type indicated above which has a chamber with first and second opposed sides. Each of the sides has an inlet port and an outlet port with an input from a different one of the fluid sources be connected to each of the inlet ports. A valve having a movable member such as a ball is mounted in each inlet port to control flow therethrough. The movable member is movable between a position where it closes the valve to block flow through the port and positions successively removed from the port where progressively greater flow through the port is permitted. A flexible membrane is mounted in the chamber between the sides to separate the chamber into two substantially isolated chamber portions. The membrane is flexed when there is a pressure differential in the chamber portions to bear against the movable member for the valve of the lower pressure chamber portion to selectively control flow through this valve. The outlet ports are connected through separate restrictors to a mixer and the valve assembly may be utilized in a high pressure SFC system, with the output from the mixer being applied to an analysis column of such system. The restrictors create a pressure in the chamber portions which vary with flow. Thus, when there is a difference in flow from the sources, the restrictor results in a pressure difference between the two chambers which is sufficient to move the membrane but is small enough that the membrane does not burst.

This pressure difference should range between a few millibars to approximately 1 bar, depending on factors such as viscosity and flow of the respective fluids. The membrane is preferably formed of a material which is substantially impervious to the fluid.

The foregoing and other objects, features and advantages of the invention will be apparent from the following more particular description of a preferred embodiment of the invention as illustrated in the accompanying drawings.

IN THE DRAWINGS

DETAILED DESCRIPTION

Figure 1:
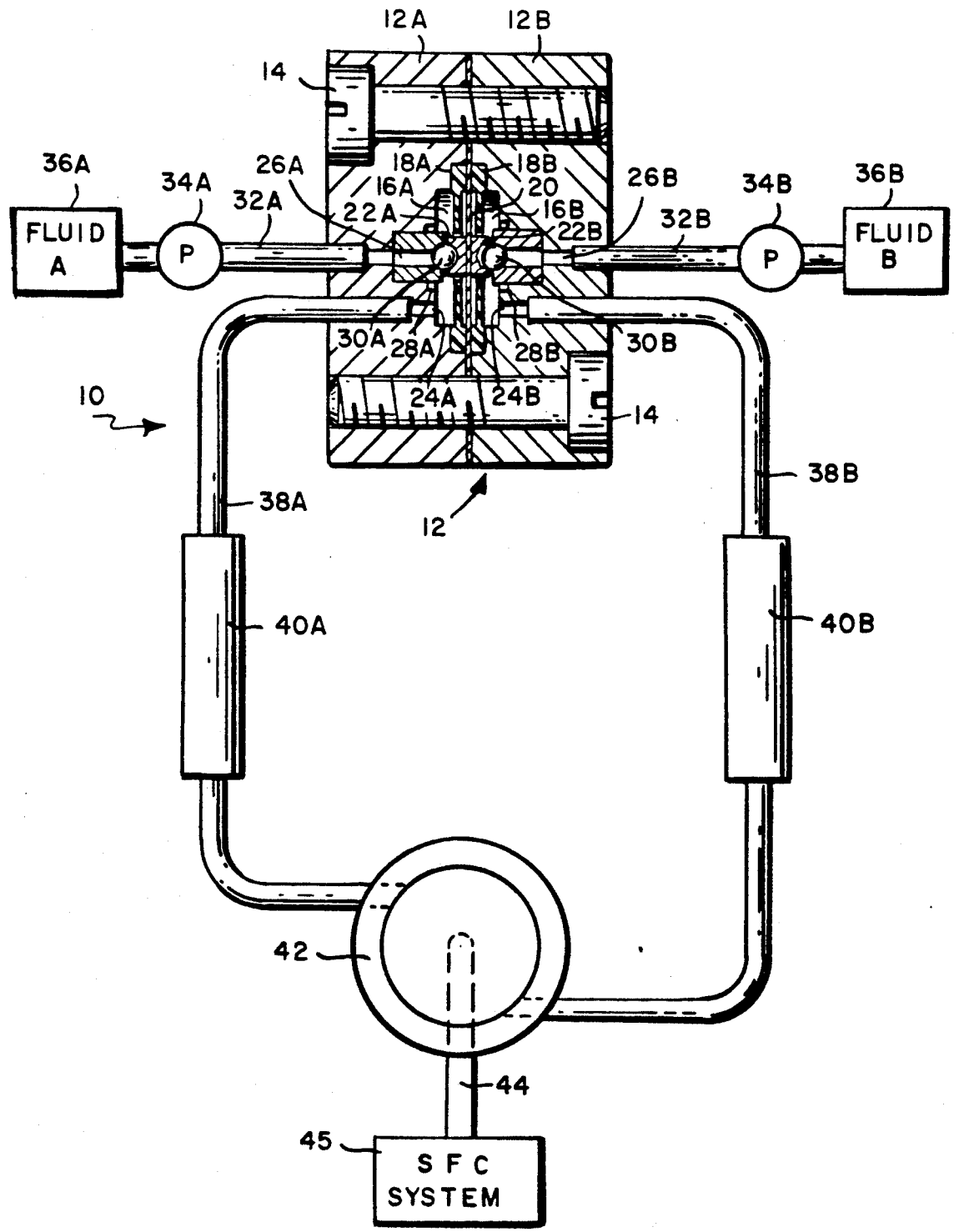
FIG. 1 is a partially cut-away side view of a valve assembly of a preferred embodiment in an equalized position with both valves partially open.

Referring to the figure, the valve assembly 10 of this invention has a high pressure housing 12 formed of two housing sections 12A and 12B which are held together by bolts 14. Housing 12 may be formed of stainless steel or of some other material, for example another metal or a ceramic, which is capable of withstanding high pressure forces. Each housing section 12A,12B has a generally circular or cylindrical indentation or chamber portion 16A,16B, respectively, formed in its inner face. When housing 12 is assembled as shown in the figure, chamber portions 16A and 16B form a high pressure chamber 16. A sealing ring 18 is seated along the perimeter of each chamber portion 16A,16B and a flexible membrane 20 is positioned between housing portions 12A and 12B when they are assembled. Membrane 20 is held in place primarily by the pressure exerted thereon by sealing rings 18A and 18B. The material for membrane 20 is selected to be impervious or substantially impervious to the liquid or gaseous fluids being utilized in the system. For a preferred embodiment, membrane 20 is a thin stainless steel disc.

Each chamber portion 16A,16B has an inlet port 22A,22B and an outlet port 24A,24B formed therein. A ball valve 26A,26B is mounted in each port 22A,22B, respectively, and is held therein by a corresponding seal 28A,28B. Ball 30A,30B for each valve is normally positioned to float away from the corresponding port, permitting flow from the port into the chamber. For a preferred embodiment, balls 30A,30B are formed of ruby and fit into sapphire seats 31A,31B.

Figure 2:
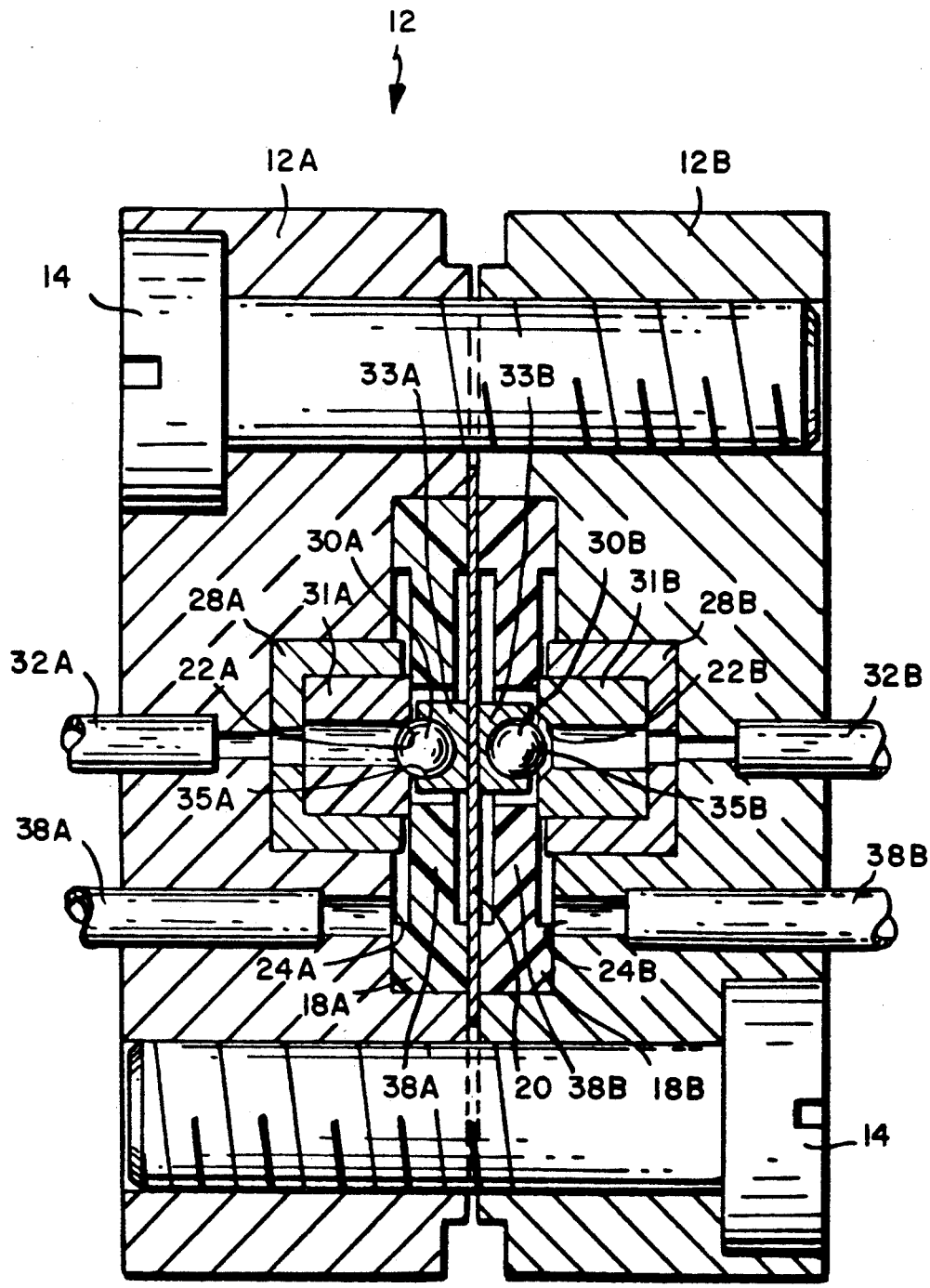
FIG. 2 is an enlarged cut-away side view of the housing portion of a valve assembly with one valve open and one closed.

As is best seen in FIG. 2, there is a cylindrical cap 33A,33B between each ball 30 and membrane 20. Each cap has a generally hemispherical opening 35 in its surface adjacent the corresponding ball 30, which opening may have slightly flattened walls and is adapted to have the corresponding ball 30 fitted therein. The ball 30 may either be tightly wedged in a corresponding opening 35 or may be loosely seated therein.

Caps 33 perform two functions. The first and primary function is to provide a larger area of contact with membrane 20 so as to avoid the potential deformation or damage which might be caused to the membrane by point contact with a ball 30. A second function is to assure that balls 30 remain properly positioned when not seated in seat 31. Since, for a preferred embodiment, membrane and ball movement is relatively small from fully seated to fully open position, in the order of 30 micrometers, the ball can be retained against movement, even in the fully open position, by contact of the ball with the membrane 20 on one side and a lip of the valve seat 31 on the other side. This is illustrated for the ball 30A in FIG. 2, which ball is in its fully open position.

As a final assurance against undesired migration of a ball 30, sealing rings 18 each have a projection 37 which extends into chamber 16 to a point closely adjacent the corresponding cap 33 to further limit lateral movement of the cap and thus of the ball seated therein.

Each inlet port 22 is connected through a pipe 32A,32B and a pump 34A,34B to a fluid source 36A,36B. Where the fluid is a gas or a liquid such as $CO_2$, it may be under pressure so that even with the pump 34 turned off, the input at the corresponding input port 22 may be pressurized. With pump 34 turned on, there is a high pressure at the corresponding input port sufficient to overcome substantial downstream restrictions (not shown).

Each output port 24 is connected through a pipe 38A,38B and a restrictor 40A,40B to one input of a mixer 42. Each restrictor 40 may be a capillary or other restriction in the corresponding pipe 38 which causes a controlled pressure buildup in the corresponding chamber portion 16 which is small (less than one bar) compared to the pressure in the system which may be up to 400 bars (6000 psi) or more. However, the restriction of a restrictor 40 should not be so great that the pressure difference in the chamber portions is sufficient to cause bursting of membrane 20. The fluids mixed under pressure in mixer 42 are outputted through a pipe 44 leading to a utilization device 45, for example, the analysis column of an SFC chromatographic system.

The dimensions of the apparatus are such that when membrane 20 is not flexed and both ball valves 26 are partially or fully open, each ball 30, as shown in FIG. 1, is in contact with membrane 20 on a lip of the corresponding seat 31, or preferably seated in cap 33 which is in contact with the membrane. When the membrane is flexed as a result of a pressure differential between chamber portions 16A and 16B, the membrane presses against the cap/ball in the lower pressure chamber portion. If the pressure differential is sufficient, the membrane induced ball movement will fully close the corresponding valve.

The valve assembly described above is adapted to solve a number of problems which may occur in the mixing of two high pressure fluids. First, the apparatus acts as an automatic shutoff valve when fluid delivery from only one of the pumps 34 is desired. Assuming, for example, that pump 34A is operating and that pump 34B is not operating, this results in fluid under pressure being applied to chamber portion 16A without fluid being delivered to chamber portion 16B. As a result of restrictor 40A, this flow difference will result in a pressure buildup in chamber portion 16A. The resulting pressure differential across membrane 20 flexes the membrane in the direction of chamber portion 16B, causing the membrane to bear against cap 33B/ball 30B. The pressure differential will become sufficient to flex the membrane a sufficient amount to cause valve 26 to become closed. Thus, to the extent that the pressure differential between the pressure in mixer 42 caused by the system and the fluid delivered from source 36A by pump 34A and the lower pressure in chamber portion 16B results in fluid from source 36A flowing from the mixer through restrictor 40B and pipe 38B into chamber portion 16B, this fluid will not be able to backflow into inlet pipe 32B or into pump 34B or fluid source 36B to which the pipe is connected.

When pump 34B resumes operation and the pressure from fluids being delivered by this pump is sufficient to overcome the force being applied by membrane 20 to cap 33B/ball 30B to close valve 26B, the pressure of fluid flowing out of port 22B will be sufficient to prevent backflow of any residual fluid in chamber portion 16B from fluid source 36A from backflowing through the inlet port and this fluid will be flushed from the chamber with the fluid from source 36B.

A second potential problem is that, even with both pumps 34 operating, there may be momentary fluctuations in fluid flow. This can cause the mix ratio in mixer 42 to have momentary variations which are undesirable. One way to overcome this problem is to buffer the excess fluid from the source having the greater flow until the flow from the other source catches up. The apparatus of this invention provides such capability.

In particular, assuming a momentary decrease in flow from pump 34B, the slight decrease in pressure in chamber portion 16B would cause membrane 20 to flex in that direction (FIG. 2), slightly increasing the size of chamber portion 16A. This permits a slightly larger volume of fluid to remain in chamber portion 16A and at the same time reduce the volume of chamber 16B which supplements some of the missing flow from this pump. When full flow from pump 34B is restored, the membrane is pushed back to its neutral position, causing the buffered fluid to be applied to the mixer as the fluid flow from source 36B increases.

The isolation of fluid from one pump to the other when there is a pressure differential between the two pumps also comes into play when pressure is being increased from one of the sources and pressure is not yet properly equalized. When pressure differentials exist sufficient to cause fluid flow from one chamber portion through the restrictors and mixer to the other chamber portion, the pressure differential in the chamber portions is also sufficient to cause membrane 20 to bear against and close the ball valve 26 in the lower pressure chamber portion. Thus, backflow is prevented in all situations.

Finally, the shutoff capability when a pressure differential exists in the system will prevent backflow from a high pressure source when both pumps 34 are turned off. Thus, if as in a typical SFC system, one source is high pressure carbon dioxide, and the other source low pressure liquid, the apparatus will prevent flow from the high pressure carbon dioxide source to the channel for the liquid source when both pumps are off. This eliminates the need for frequent priming of the liquid channel pump.

A simple apparatus is thus provided which controls high pressure fluid flow from two separate sources, eliminating numerous potential sources of backflow from one channel to the other. While the invention has been particularly shown and described above with reference to a preferred embodiment, it should be understood that the foregoing and other changes in form and detail may be made therein by one skilled in the art without departing from the spirit and scope of the invention.

What is claimed is:

1. A valve assembly for controlling pressurized inputs from two separate fluid sources comprising:

a chamber having first and second opposed sides;
    an inlet port and an outlet port on each of said sides;
    means for connecting an input from a different one of said sources to each of said inlet ports;
    a valve having a movable member mounted on each inlet port to control flow through the port, the movable member being movable between a position where it blocks fluid flow through the port and a plurality of positions successively removed from the port where progressively greater flow through the port is permitted;
    a flexible membrane mounted in the chamber between the sides to separate the chamber into two substantially isolated chamber portions, the membrane being flexed when there is a pressure differential in the chamber portions to bear against the movable member for the valve of the lower pressure chamber portion to selectively control the position of the movable member and thus the flow through said valve; and
    first and second restrictors connected to the outlet ports in said first and second sides, respectively.

2. A valve assembly as claimed in claim 1 including a mixer, and means for connecting outputs from said restrictors as inputs to said mixer.

3. A valve assembly as claimed in claim 2 wherein said assembly is being utilized in a high pressure SFC system, and including means for connecting the output of the mixer to said SFC system.

4. A valve assembly as claimed in claim 2 wherein, when the pressure differential between a first higher pressure one of said chamber portions and a second lower pressure chamber portion exceed a predetermined threshhold, fluid from the source connected to the first chamber input port may flow through the restrictor connected to the first chamber portion outlet, the mixer and the other restrictor to the second chamber portion, and wherein said membrane and valves are selected and positioned such that the valve in the inlet port for the second chamber portion is closed before the pressure differential reaches said threshhold, whereby backflow of fluid from one source to the other is prevented.

5. A valve assembly as claimed in claim 1 wherein said restrictors result in a controlled pressure buildup in said chamber portion, but permit sufficient fluid flow from the chamber portion so that the pressure difference between the chamber portions is not sufficient to burst the membrane.

* * * * *